United States Patent [19]
Woodbridge et al.

[11] Patent Number: 4,550,077
[45] Date of Patent: Oct. 29, 1985

[54] β-AMYLASE DETERMINATION

[75] Inventors: J. Eliot Woodbridge, Princeton, N.J.; George F. Bulbenko, Langhorne, Pa.; J. John Marshall, Miami, Fla.

[73] Assignee: Electro-Nucleonics, Inc., Fairfield, N.J.

[21] Appl. No.: 147,473

[22] Filed: May 7, 1980

[51] Int. Cl.[4] .................. C12Q 1/40; C12Q 1/32; C12Q 1/28; C12P 19/14
[52] U.S. Cl. .................... 435/22; 435/14; 435/18; 435/26; 435/28; 435/202; 435/203; 435/204; 435/99; 435/810
[58] Field of Search .............. 23/230 B; 435/14, 18, 435/22, 26, 28, 202, 203, 204, 810, 99

[56] References Cited

U.S. PATENT DOCUMENTS

| | | | |
|---|---|---|---|
| 3,788,946 | 1/1974 | Kurimoto et al. | 435/22 |
| 3,879,263 | 4/1975 | Adams | 435/14 |
| 4,000,042 | 12/1976 | Adams | 435/22 |
| 4,009,079 | 2/1977 | Tsujino et al. | 435/22 |
| 4,036,697 | 7/1977 | Pierre et al. | 435/22 |
| 4,052,226 | 10/1977 | Verbanac | 435/96 |
| 4,102,747 | 7/1978 | Driscoll et al. | 435/22 |
| 4,172,765 | 10/1979 | Keyes | 435/22 |
| 4,268,628 | 5/1981 | Klose et al. | 435/22 |
| 4,304,854 | 12/1981 | Nix et al. | 435/22 |

FOREIGN PATENT DOCUMENTS 0005867 6/1978 European Pat. Off. .............. 435/22

OTHER PUBLICATIONS

Huang, et al., "A Specific Sensitive Assay for α-Amylase Utilizing Modified Starch as Substrate", *Clin. Chem.*, vol. 22, No. 7 (1976), p. 1164.

Nix, et al., "A New Method for Determination of α-Amylase, *Clin. Chem.*, vol. 24, No. 6, (1978), p. 1000.

Madappally et al., "Enzymatic Determination of Serum Amylase," *Clin. Chem.*, vol. 22, No. 7, (1976), p. 1000

Clinica Chimica Acta, 76, (1977), pp. 277–283, by J. John Marshall et al.

*Primary Examiner*—Thomas G. Wiseman
*Attorney, Agent, or Firm*—Elliot M. Olstein

[57] ABSTRACT

A reagent suitable for α-amylase determinations. The reagent contains a modified, blocked amylaceous polysaccharide substrate, e.g., starch glyolate, an exating by amylose, a buffer and an enzymatic glucose measuring system. The glycolate substrate is selected such that the ratio of methylated glucose to glucose is between 1:4 to 1:16. The system permits an impid assay in a single vid within 7 minutes and can be automated.

19 Claims, 1 Drawing Figure

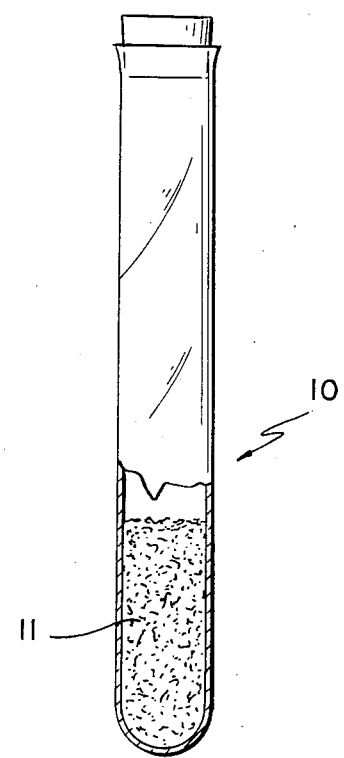

β-AMYLASE DETERMINATION

This invention relates to α-amylase determination.

Determination of α-amylase in a body fluid, in particular, serum, can be used for the diagnosis and confirmation of acute pancreatitis. Extremely elevated levels of α-amylase (2½ times the upper limit of normal) are usually only found in acute pancreatitis; however, several other conditions such as biliary colic, perforated gall bladder, pneumonia, perforated appendix or perforated ulcer of the stomach, duodenum or ileum will also produce increased α-amylase activity in serum and urine.

The present invention is directed to a new and improved reagent, reagent package and method for determining amylase.

In accordance with one aspect of the present invention, there is provided a reagent or kit for α-amylase determination comprised of an amylaceous polysaccharide modified to include blocking groups which do not substantially prevent cleavage by α-amylase and which prevent an α-amylase-free exo-acting amylase from acting on the polysaccharide; an enzyme or enzyme mixture which includes an α-amylase-free exo-acting amylase which releases glucose from the cleaved polysaccharide; buffer free of enzyme inhibitor; and an enzymatic glucose rate detector. The components are present in an amount effective for α-amylase determination.

In accordance with another aspect of the present invention, there is provided a reagent package for determination of α-amylase comprised of a container and a dry mixture in the container comprised of an amylaceous polysaccharide modified to include blocking groups which do not prevent cleavage by α-amylase and which prevent an α-amylase-free exo-acting amylase from acting on the polysaccharide; an enzyme or enzyme mixture which includes an α-amylase-free exo-acting amylase which releases glucose from the cleaved polysaccharide; buffer free of enzyme inhibitor; and an enzymatic glucose rate detector. The components are presented in an amount effective for α-amylase determination.

In accordance with a further aspect of the present invention, there is provided a method for determining α-amylase by mixing an amylase-containing sample with an amylaceous polysaccharide modified to include blocking groups which do not prevent cleavage by α-amylase and which prevent an α-amylase-free exo-acting amylase from acting on the polysaccharide; an enzyme or enzyme mixture which includes an α-amylase-free exo-acting amylase which releases glucose from the cleaved polysaccharide; buffer free of enzyme inhibitor; an enzymatic glucose rate detector, and subsequently measuring absorption at one or more time intervals or continuously to thereby determine amylase.

In accordance with the present invention, the blocked polysaccharide substrate is unblocked by the action of α-amylase, and the unblocked polysaccharide substrate releases glucose by the action of the enzyme. The rate of glucose production provides a measure of α-amylase activity and, accordingly, such α-amylase activity can be determined by measuring the rate of glucose production. Thus, in accordance with the present invention, α-amylase is determined by providing and using a reagent which includes the blocked amylaceous polysaccharide, enzyme as hereinabove described, buffer, and an enzymatic glucose rate detector.

The amylaceous polysaccharide substrate is modified to include blockages to the action of the enzyme; e.g., glucoamylase, whereby the enzyme will not hydrolyze such polysaccharide; however, in the presence of α-amylase, there are internal cleavages of the chains to expose chain ends on which the exo-acting enzyme can act. As representative examples of suitable amylaceous polysaccharides, there may be mentioned starch (potato starch, corn starch, wheat starch, rice starch, tapioca, glycogen, etc.), or purified starch fractions (amylose, amylopectin) and the like. A partially hydrolyzed starch is a preferred substrate, e.g., partially hydrolyzed potato starch. Such amylaceous polysaccharides may be modified to provide blockages to the action of glucoamylase by procedures known in the art. Thus, for example, such blockages can be introduced by limited periodate oxidation; by substitution; for example, carboxymethylation, esterification (with acids, acid anhydrides, acid chlorides); hydroxyethylation with ethylene oxide and other procedures known in the art. The preferred substrate is carboxymethylated starch (starch glycolate). The method of blocking the polysaccharide is coordinated with the polysaccharide so as to provide for solubility in the test media (generally water), with the blocking not being effected to a degree which would prevent action by α-amylase and subsequent glucose release.

In employing carboxymethylated starch as the substrate, in order to provide solubility and sufficient available glucose for the assay, in general, the ratio of carboxy methylated glucose to glucose in the starch is from 1:4 1:16, with a ratio of from 1:6 to 1:10 being preferred. In preparing the blocked substrate, subsequent to the blocking, the blocked substrate is reacted with the enzyme to be used in the assay reagent kit to degrade any unblocked glucose segments susceptible to action of the enzyme without prior action of α-amylase.

The enzyme employed in the kit is an enzyme or enzyme mixture which is free of α-amylase and which includes an exo-acting amylase which converts the α-amylase cleaved polysaccharide to glucose. A particularly preferred enzyme is α-amylase-free glucoamylase. Another suitable enzyme is an α-amylase-free mixture of β-amylase and a maltase preferred α-amylase free glucoamylase is available from Biscayne Biochemical Laboratories in Miami, Fla. Miles Laboratories also sells an α-amylase free glucoamylase.

The buffer, as hereinabove noted, is one which is free of an enzyme inhibitor so as to permit continuation of enzymatic activity for the rate measurement employed for determining amylase. The buffer generally includes an α-amylase activator; e.g., chloride ions. The buffer should be one which maintains a pH in the order of from 5.0 to 9.0, and preferably from 6.0 to 7.5. The pH is selected to optimize the enzyme activity and in view of the fact that four enzymes participate in the assay, the selected pH is generally a compromise between the best pH for each of the enzymes. A preferred buffered pH is 6.9. As representative examples of suitable buffers, there may be mentioned: β-glycerophosphate, 3-(N-Morpholino) propane sulfonic acid (MOPS), N-2-hydroxyethylpiperazine-N′-2-ethane sulfonic acid (HEPES), N-2-acetamide-2-aminoethanesulfonic acid (ACES), imidazole and others.

The enzymatic glucose rate detector is one which can provide a measurement of the rate of glucose production. A preferred glucose rate detector is a glucose-hexokinase detector system, with such detector system including adenosine triphosphate (ATP), β-nicotinamide-adenine dinucleotide (NAD); hexokinase; and glucose-6-phosphate dehydrogenase (G-6-PDH). The enzymatic reactions are represented by the following:

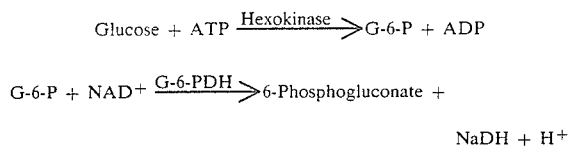

$$\text{Glucose} + \text{ATP} \xrightarrow{\text{Hexokinase}} \text{G-6-P} + \text{ADP}$$

$$\text{G-6-P} + \text{NAD}^+ \xrightarrow{\text{G-6-PDH}} \text{6-Phosphogluconate} + \text{NaDH} + \text{H}^+$$

Wherein ADP is adenosinediphosphate, G-6P is glucose-6-phosphate, and NADH is the reduced form of β-nicotinamide-adenine dinucleotide.

Another representative glucose rate detection system employs glucose oxidase and peroxidase, as disclosed, for example by Trinder, J. Clin. Path., 22, 246 (1969).

NADH absorbs light at 340 nm, while NAD does not, and the rate at which NADH is evolved is directly proportional to the increase in absorbance of light at 340 nm at constant temperature, usually in the range of 15° to 50° C., and constant pH. The rate of formation of NADH is proportional to the rate at which glucose is evolved, which in turn is proportional to α-amylase concentration in the sample, whereby the increase in absorbance at 340 nm can be used as a direct measure of the original concentration of α-amylase in the sample. It is to be understood that a wavelength other than 340 nm could be employed.

In accordance with the preferred embodiment of the present invention, the hereinabove described four components of the α-amylase determining reagent are provided as a mixture, preferably a dry mixture, and such dry mixture can be suitably packaged in a single vial. The reagents, if dry, are reconstituted in water for the α-amylase assay. It is to be understood, however, that the reagent kit may include separate vials of each of the reagents or separate vials which include more than one reagent instead of an intimate mixture of all reagents in a single vial or container. An advantage of the present invention, however, is that the reagents can be premixed in the kit in a single vial or container, preferably as a dry mixture.

In accordance with the assay of the present invention, a sample containing α-amylase, such as a serum sample, is added to an aqueous mixture of the blocked amylaceous polysaccharide, enzyme of the type hereinabove described, buffer free of enzyme inhibitor and enzymatic glucose rate detector, with the α-amylase causing the hydrolysis of the unblocked portions, with the exo-acting enzyme immediately acting on the resulting non-reducing chain ends to release glucose molecules. The glucose released is measured by the enzymatic glucose rate detector, and the rate of glucose production is directly related to the α-amylase activity of the sample. In this manner, α-amylase can be rapidly detected in a simplified procedure which involves only addition of a sample containing α-amylase to a reagent solution, followed by appropriate measurement of α-amylase activity by measuring the rate of glucose release.

The invention will be further described with respect to the following drawing, wherein:

The drawing is an embodiment of a reagent package for determining α-amylase.

Referring to the drawing, there is shown a reagent vial, schematically designated as 10, which includes dry α-amylase reagent, schematically generally indicated as 11, with such α-amylase reagent being comprised of blocked amylaceous polysaccharide as hereinabove described; enzyme for releasing glucose from the amylaceous polysaccharide subsequent to cleaving thereof by α-amylase, as hereinabove described; buffer free of enzyme inhibitor; and an enzymatic glucose rate detector.

Thus, for example, the dry α-amylase reagent may be formulated as follows, in an amount to give on reconstitution with distilled or deionized water the following nominal concentrations:

| | |
|---|---|
| Carboxymethylated Starch | 2.3 g/liter |
| Sodium Glycerophosphate | 50 mmol/liter |
| Calcium Chloride | 5 mmol/liter |
| ATP | 1.3 mmol/liter |
| NAD | 1.3 mmol/liter |
| Magnesium Ion | >12 mmol/liter |
| Hexokinase (yeast) | >3 ku/liter |
| α-amylase-free Glucoamylase (microbial) | >3 ku/liter |
| G-6-PD (L.mesenteroides) pH 6.9 | >3 ku/liter |

The carboxymethylated starch employed in the kit is preferably prepared as follows:

A suspension of one gram Hydrolysed Starch, Catalog No. 2901-02-7, manufactured by Connaught Laboratories, Ltd., 1755 Steeles Avenue, W., P.O. Box 1755, Willowdale, Ontario, Canada, in 16 ml deionized water containing 0.20 g sodium chloride and 1.5 g sodium hydroxide, is warmed to 50° C., allowed to react with 0.47 g sodium monochloroacetate, and kept at 50° C. for 3 hours. The solution is dialyzed for 24 hours against water, treated with acetic acid to adjust to pH 4.3±0.2, then incubated for 3 hours at 37° C. in the presence of 1,100 U of glucoamylase (*Aspergillus niger:* amylase-free). After dialysis of 72 hours against water, the substrate solution is lyophilized and stored refrigerated at 4°-8° C.

The α-amylase free glucoamylase is obtained from Biscayne Biochemical Laboratories in Miami, Fla.

Thus, for example, vial 10 may be either a 3 ml or a 16 ml vial, which when reconstituted with 3 ml or 16 ml of deionized water, respectively, provides the hereinabove described nominal concentrations. It is to be understood, however, that other suitable vial amounts may be employed.

The following is a test procedure for determining α-amylase using a 3 ml reagent vial having the hereinabove described components:

1. Reconstitute dry contents of tube with 3.0 ml of distilled or deionized water. Gently invert to solubilize contents.
2. Transfer contents to a cuvet and warm to 37° C.
3. Add 0.01 ml of serum.
4. Incubate 5 minutes at 37° C.
5. Measure the average change in absorbance per minute (ΔA/min) at 340 nm, taking readings at convenient time intervals. The temperature must be held constant in the cuvet. Measure against a water blank.

NOTE: A highly elevated Amylase (ΔA/min=0.200 or greater) may exhaust the substrate before measurement can be taken. In this instance, dilute the sample with saline and multiply the results by the dilution factor.

RESULTS

Units—One α-amylase unit (U) is the amount of α-amylase that is necessary to cause the hydrolysis of one micromole of glucosidic linkages in the blocked starch per minute at 37° C.

U/liter = $\Delta A$/min × K-factor

U/liter@340 nm = $\Delta A$/min × 12,100

U/liter@366 nm = $\Delta A$/min × 22,800

U/liter@334 nm = $\Delta A$/min × 12,550

EXAMPLE

| | |
|---|---|
| Creep rate of reagent | 0.002/min |
| Serum volume | 0.01 ml |
| Reaction volume | 3.01 ml |
| 5 min Absorbance reading @ 340 nm | 0.582 |
| 7 min Absorbance reading @ 340 nm | 0.716 |
| Reaction temperature | 37° C. |

$$\Delta A/\text{min} = \frac{0.716 - 0.582}{2} = 0.067$$

True $\Delta A$/min = 0.067 − 0.002 = 0.065
U/liter = 0.065 × 12,100 × 1 = 786.5

DERIVATION OF FORMULA $$U/\text{liter} = \frac{\Delta A/\text{min} \times 10^6 \times \text{total reaction volume}}{\text{molar absorptivity} \times \text{ml of serum} \times \text{lightpath} \times 4}$$

$$= \frac{\Delta A/\text{min} \times 10^6 \times 3.01}{6.22 \times 10^3 \times 0.01 \times 1.0 \times 4}$$

$$= \Delta A/\text{min} \times 12,100$$

when
A/min = change in absorbance per minute
$10^6$ converts moles to micromoles.
Lightpath = 1.0 cm
4 = approximate number of molecules of glucose formed per scission of starch molecule.
$6.22 \times 10^3$ = molar absorptivity for NADH at 340 nm.

When testing at a wavelength other than 340 nm, the proper molar absorptivity value must be substituted for $6.22 \times 10^3$. The molar absorptivity for NADH at 366 nm = $3.3 \times 10^3$ and at 334 nm = $6.0 \times 10^3$.

The present invention is particularly advantageous in that there is provided a new and improved reagent, and reagent package, as well as a method, which permits the rapid assay of α-amylase in a single vial, which can be adapted to automation. Thus, the assay can be conducted in a time period in the order of 7 minutes with a minimum amount of assay steps.

These and other advantages should be apparent to those skilled in the art from the teachings herein.

Although the present invention is particularly applicable to the determination of α-amylase in physiological fluids, the scope of the invention is not so limited. For example, the invention has applicability to determination of α-amylase in plant extracts, microbial culture filtrates, etc.

Numerous modifications and variations of the present invention are possible in light of the above teachings and, therefore, within the scope of the appended claims, the invention may be practised otherwise than as particularly described.

We claim:

1. A reagent kit for the determination of alphaamylase, comprising:
   a. a water soluble carboxymethylated starch which is cleaved by alpha-amylase and which is not acted on by an exo-acting amylase, said water soluble carboxymethylated starch being present in an amount effective to determine alpha-amylase by measuring rate of glucose released after cleavage by alpha-amylase and enzymatic release of glucose by an exo-acting amylase;
   b. an (enzyme or) enzyme mixture including an exo-acting amylase which is free of alpha-amylase and which is capable of and is present in an amount effective for releasing glucose from alpha-amylase cleaved carboxymethylated starch to determine alpha-amylase by measuring the rate of glucose production, said enzyme mixture containing β-amylase and a maltase which is free of alpha-amylase;
   c. a buffer for maintaining pH for alpha-amylase determination, said buffer being free of enzyme inhibitor which would interfere with enzymatic activity for releasing glucose; and
   d. enzymatic reagent for detecting rate of glucose formation, said enzymatic reagent being present in an amount effective for determining alpha-amylase by measuring the rate of glucose production, wherein said components (a), (b), (c) and (d) are present in an amount effective for a rate determination of alpha-amylase.

2. The K.t of claim 1 wherein component (d) is a glucose hexokinase rate detector, comprising adenosine triphosphate, nicotinamide adenine dinucleotide, hexokinase, and glucose-6-phosphate dehydrogenase.

3. The K.t of claim 2 wherein component (c) maintains a pH of from 5.0 to 9.0 in the media for α-amylase determination.

4. The K.t. of claim 3 wherein component (c) is comprised of at least one member selected from the group consisting of imidazole, β-glycerophosphate, 3-(N-morpholino)propane sulfonic acid, and N-2-acetamide-2-aminoethanesulfonic acid.

5. A reagent kit for the determination of α-amylase, comprising:
   a. a water soluble carboxymethylated starch which is cleaved by α-amylase and which is not acted on by an exo-acting amylase, said water soluble carboxymethylated starch having a ratio of carboxymethylated glucose to glucose of from 1:4 to 1:16 and being present in an amount effective to determine α-amylase by measuring rate of glucose released after cleavage by α-amylase and enzymatic release of glucose by an exo-acting amylase;
   b. an enzyme or enzyme mixture including an exo-acting amylase which is free of α-amylase and which is capable of and is present in an amount effective for releasing glucose from α-amylase cleaved carboxymethylated starch to determine α-amylase by measuring the rate of glucose production;
   c. a buffer for maintaing pH for α-amylase determination, said buffer being free of enzyme inhibitor which would interfere with enzymatic activity for releasing glucose; and
   d. enzymatic reagent for detecting rate of glucose formation, said enzymatic reagent being present in an amount effective for determining α-amylase by measuring the rate of glucose production, wherein said components (a), (b), (c) and (d) are present in an amount effective for a rate determination of α-amylase.

6. The kit of claim 5 wherein component (b) is glucoamylase which is free of α-amylase.

7. The kit of claim 6 wherein components (a), (b), (c) and (d) are in the form of a mixture.

8. The kit of claim 7 wherein the mixture is a dry mixture.

9. The kit of claim 8 wherein component (d) is a glucose-hexokinase rate detector, comprising adenosine triphosphate, nicotinamide adenine dinucleotide, hexokinase, and glucose-6-phosphate dehydrogenase.

10. The kit of claim 9 wherein the component (c) maintains a pH of from 5.0 to 9.0 in the media for α-amylase determination.

11. The kit of claim 10 wherein component (c) is comprised of at least one member selected from the group consisting of imidazole, β-glycerophosphate, 3-(N-morpholino)propane sulfonic acid, N-2-hydroxyethylpiperazine-N'-2-ethanesulfonic acid, and N-2-acetamide-2-aminoethanesulfonic acid.

12. The kit of claim 5 wherein component (d) is a glucose oxidase-peroxidase glucose rate detector.

13. The kit of claim 6 wherein component (d) is a glucose-hexokinase rate detector, comprising adenosine triphosphate, nicotinamide adenine dinucleotide, hexokinase, and glucose-6-phosphate dehydrogenase.

14. The kit of claim 13 wherein component (c) is comprised of at least one member selected from the group consisting of imidazole, β-glycerophosphate, 3-(N-morpholino)propane sulfonic acid, N-2-hydroxyethylpiperazine-N'-2-ethanesulfonic acid, and N-2-acetamide-2-aminoethanesulfonic acid.

15. A reagent package for determination of α-amylase, comprising:
   a container and a dry mixture in the container, comprising:
   a. a water soluble carboxymethylated starch which is cleaved by α-amylase and which is not acted on by an exo-acting amylase, said water soluble carboxymethylated starch having a ratio of carboxymethylated glucose to glucose of from 1:4 to 1:16 and being present in an amount effective to determine α-amylase by measuring rate of glucose released after cleavage by α-amylase and enzymatic release of glucose by an exo-acting amylase;
   b. an enzyme or enzyme mixture including an exo-acting amylase which is free of α-amylase and which is capable of and is present in an amount effective for releasing glucose from α-amylase cleaved carboxymethylated starch to determine α-amylase by measuring the rate of glucose production;
   c. a buffer for maintaining pH for α-amylase determination, said buffer being free of enzyme inhibitor which would interfere with enzymatic activity for releasing glucose; and
   d. enzymatic reagent for detecting rate of glucose formation, said enzymatic reagent being present in an amount effective for determining α-amylase by measuring the rate of glucose production, wherein said components (a), (b), (c) and (d) are present in an amount effective for a rate determination of α-amylase.

16. An assay for the determination of α-amylase, comprising:
   mixing a sample containing α-amylase and the reagent kit containing:
   a. A water soluble carboxymethylated starch which is cleaved by alpha-amylase and which is not acted on by an exacting amylase, said water soluble carboxymethylated starch being present in an amount effective to determine alpha-amylase by measuring rate of glucose by an oxoacting amylase;
   b. An (enzyme or) enzyme mixture including an exacting amylase which is to free of alpha-amylase and which is capable of and is present in an amount effective for releasing glucose form alpha-amylase cleaved carboxymethylated starch to determine alpha-amylase by measuring the rate of glucose production, said enzyme mixture containing α-amylase and a maltase which is free of alpha-amylase:
   c. A buffer for maintaining pH for alpha-amylase determination, said buffer being free of enzyme inhibitor which would interfere with enzymatic activity for releasing glucose; and
   d. Enzymatic reagent of detecting rate of glucose formation, said enzymatic reagent begin present in an amount effective for determining alpha-amylase by measuring the rate of gluycose production, wherein said components (a), (b), (c) and (d) are present in an amount effective for a rate determination of alpha-amylase, incubating the mixture, to unblock the starch by action of α-amylase, release glucose by the action of said enzyme or enzyme mixture and indicate glucose production by the enzymatic reagent; and measuring the rate of glucose production to determine α-amylase in the sample.

17. The assay of claim 16 wherein said enzyme for release of glucose is glucoamylase which is free of α-amylase.

18. The assay of claim 17 wherein the enzymatic glucose rate detector is a glucose-hexokinase rate detector, comprising adenosine triphosphate, nicotinamide adenine dinucleotide, hexokinase, and glucose-6-phosphate dehydrogenase.

19. The assay of claim 18 wherein the buffer is comprised of at least one member selected from the group consisting of imidazole, β-glycerophosphate, 3-(N-morpholino)propane sulfonic acid, N-2-hydroxyethylpiperazine-N'-2-ethanesulfonic acid, and N-2-acetamide-2-aminoethanesulfonic acid.

* * * * *